United States Patent [19]
De Luca et al.

[11] Patent Number: 4,960,759
[45] Date of Patent: Oct. 2, 1990

[54] PHARMACOLOGICAL USE OF URIDINE IN THE TREATMENT OF NERVOUS DISORDERS

[75] Inventors: Giovanna De Luca; Giovanni Di Stazio; Mario Materazzi; Vincenzo Politi, all of Rome, Italy

[73] Assignee: Polifarma S.P.A., Rome, Italy

[21] Appl. No.: 367,615

[22] Filed: Jun. 19, 1989

[30] Foreign Application Priority Data

Jun. 21, 1988 [IT] Italy ................................ 48118 A/88

[51] Int. Cl.$^5$ ............................................ A61K 31/70
[52] U.S. Cl. ...................................................... 514/50
[58] Field of Search ........................................... 514/50

[56] References Cited
FOREIGN PATENT DOCUMENTS 0178267 4/1986 European Pat. Off. .

OTHER PUBLICATIONS

Hokfelt et al., Evidence for Coexistence of Dopamine and CCK in Mesa-Limbic Neurones., Nature, 285, 476–478 (June 1980).
Herbert Y. Meltzer, M. D., Psychopharmacology, Raven Press, 1987, pp. 721–722, 736–737, 1137–1138 and 1258–1260.
Robert George et al., Annual Review of Pharmacology and Toxicology, 23, 7–9, 116. (May 1983).
Chem. Abst., 104–122947a, (1986).

Primary Examiner—Stanley J. Friedman
Attorney, Agent, or Firm—Birch, Stewart, Kolasch & Birch

[57] ABSTRACT

Disorders due to an altered balance of dopamine release by the cerebral dopaminergic system, such as schizophrenia and Parkinson's disease, can be treated by administration of uridine which is a specific agent for the protection of the cholecystokinin level in the brain tissue.

6 Claims, No Drawings

PHARMACOLOGICAL USE OF URIDINE IN THE TREATMENT OF NERVOUS DISORDERS

BACKGROUND OF THE INVENTION

1. Field of the Invention

The present invention relates to neuropharmacology and in particular to the pharmacological use of uridine in the treatment of those nervous disorders due to a modified dopaminergic balance, such as schizophrenia and Parkinson's disease.

2. Description of the Prior Art

It is already known in the state of the art (reference is made to the European published application number 0178267) that an administration of uridine has a protective effect on certain cerebral hormonal peptides, in particular somatostatin and cholecystokinin, when an insulinic hypoglycemia is induced in rat in an animal pathology pattern.

Cholecystokinin (CCK) is a hormonal peptide having 33 aminoacid residues, which acts in various manners both on the gastro-intestinal tract, and on the central nervous system (CNS) of mammals.

Psychopharmacology, Raven Press, 1987, Chapter 130, pages 1258–1260 describes that at the intestine level CCK produces contraction of the gall bladder, decrease of gastric emptying, and stimulation of pancreatic enzyme secretion. Systemic injection of CCK produces a potent dose-related suppression of feeding in a wide variety of animals, including monkeys. In humans, intravenous infusion of CCK reduces food intake both in obese and lean subjects.

It is also known in the state of the art (Ann. Rev. Pharmacol., 23, 7–9, 1983) that at the CNS level, CCK appears to act through its octapeptide fragment, denominated CCK-8, which appears to be present mainly in cerebral areas, such as cortex, hyppocampus, amigdala and hypothalamus. Particularly in the cortex, CCK appears to be the most widespread hormonal peptide.

Furthermore, it has been known in the state of the art for some years (see Nature 285, 476–478, 1985) that the hormonal peptides present in CNS are almost always associated to classic neurotransmitters (catecholamine, serotonine, gaba, and the like) presumably for modulating their physiologic activity on neurons.

In particular CCK was found almost always associated to dopamine, which is one of the most important catecholamines of CNS.

Dopamine is in fact one of the most important neurotransmitters, and it is known that an altered balance thereof produces serious psychic disorders, such as schizophrenia and psychomotive disorders, such as Parkinson's disease.

The discovery that CCK results to be always associated to dopamine has stimulated a lot of studies on the interactions between CCK and dopamine, on the basis of which the belief has been obtained that CCK acts as neuromodulator with respect to dopamine, in that:

(a) CCK can activate the hyperpolarized dopaminergic neurons;

(b) CCK can increase the activity of dopaminergic neurons, namely the dopamine producing neurons, in the areas in which both CCK and dopamine exist together (dopamine will be hereinafter shortened into DA);

(c) CCK is able to induce a tonic state of inactivation in certain dopaminergic neurons;

(d) it is able to enhance the inhibition of dopaminergic neurons induced by low doses of apomorphine (see Pharmacol., page 116).

As a consequence according to the state of the art, CCK has been considered as a possible drug for treating schizophrenia, in view of its recognized properties of modulating the dopaminergic receptor.

In fact, whereas it is still uncertain whether schizophrenia can be considered a single disease as far as a single etiology and a single optimal treatment are concerned, in the last ten years a considerable therapeutic progress has been made by the development of ever more selective drugs.

The results of the first tests using chlorpromazine had caused to be accepted the evidence that all the neurolectics developed in the past reduced psychosis through a block of the DA receptors. However, this treatment often resulted in acute and chronic side effects, which in humans were manifested by Parkinson type tremors and tardive dyskinesia.

Consequently the strategy was followed of developing new antipsychotic drugs by using the selective antagonism on certain receptor sites of DA. This has been possible in that in the last years more and more information has been obtained concerning the central dopaminergic system, its anatomy, biochemistry and physiology, along with its multiple capability of interaction with other neurotransmitters.

CCK-8 was therefore supposed to be a possible drug of new type for schizophrenia, both in that it is mainly located at the cortex level, and in that it is located together with DA in mesencephalic dopaminergic neurons. As is described in the abovementioned Psychopharmacology, on pages 721–722, as well as 736–737 and 1137–1138, CCK-8 has been tested for its antipsychotic action in schizophrenic subjects by some Japanese students. This initial study referred that CCK-8 was a rather powerful antipsychotic.

Preclinical studies were then undertaken to investigate efficiency and mechanism of action of CCK-8. Whereas these studies are at present under prosecution, confirming a strong action of CCK-8 in schizophrenia, however, the controlled clinical tests successively carried out have been consistanly negative. Not only psychosis, but also other centrally mediated functions, such as visual evoked potential and involuntary movements in the patients failed to change with CCK-8. The peptide also fails to alter the symptoms in severely affected Parkinson's disease patients. On the other hand, in animal models and in vitro experiments, CCK-8 modulates the release of DA from nerve terminals. These central actions occur in rats when CCK is injected directly into the brain or it is placed in contact with the tissues. An explanation of the negative clinical results of CCK-8 in the treatment of schizophrenia is that the peptide fails to enter the brain with systemic administration, as it has been evidenced in tests with monkeys, in that it is not able to cross the blood-brain barrier.

This results in the conclusion that an improvement of psychosis in schizophrenia cannot be obtained by administration of CCK.

SUMMARY OF THE INVENTION

It has now been surprisingly found, according to the invention, that an adminsitration of uridine produces the effect that an administration of CCK fails to produce, i.e. the effect of controlling the function of the dopaminergic system.

According to the invention it is possible to carry out a treatment of psychic disorders of schizophrenic and Parkinson's disease type, by means of administration of uridine to subjects suffering from an altered functioning of the dopaminergic system. It is consequently an object of the invention the use of uridine in pharmaceutic formulations for the above mentioned indication.

Pharmacological tests supporting the abovementioned use are described hereinafter.

1. Test on cerebral ageing

The test herein described shows that an administration of uridine has a selective effect on the protection of CCK in cerebral ageing.

To this end uridine was administered for six months to adult rats. It is known that during ageing many neurotransmitters and neurohormones are produced in CNS in much more reduced amounts, both because a considerable aspecific loss of neurons occurs, and in view of particular metabolic and circulatory problems. Among others, also cerebral hormonal peptides somatostatin and CCK undergo a wide fall during ageing.

This test was evaluating the effect on rats chronically treated with uridine with respect to the protection from somatostatin and CCK fall during physiologic ageing.

Twenty male rats CD aged six months were treated for six months with uridine. The substance was dissolved into the drinking water in a 0.5 mg/ml concentration. In average, the rats assumed 12.5 mg per day.

Upon reaching one year of age, the animals were sacrificed and the brains sliced and treated with immunocytochemical reactives, following the method described in Acta Physiologica Scandinavica, Supplementum 532, 1984.

The results, expressed in comparison to somatostatin and CCK values found in rats having the same age, maintained in the same conditions, but not treated with uridine, are shown in the following Table 1.

TABLE 1

Effect of chronical treatment with uridine on rats 12,5 mg/die per os on immunoreactivity from somatostatin (SRIF) and cholecystokinin (CCK)

| | (arbitrary units) | | | |
| --- | --- | --- | --- | --- |
| | SRIF | | CCK | |
| Cerebral Area | Controls | Uridine | Controls | Uridine |
| FrPa | 83 ± 8 | 78 ± 3 | — | — |
| CPu | 100 ± 5 | 92 ± 8 | 102 ± 8 | 95 ± 10 |
| PoA | 90 ± 10 | 83 ± 3 | 168 ± 12 | 275 ± 25** |
| SCh | 280 ± 20 | 243 ± 33 | — | — |
| Arch | 290 ± 20 | 315 ± 35 | — | — |
| Hip | 85 ± 15 | 80 ± 5 | 105 ± 5 | 175 ± 25** |
| VM | 185 ± 15 | 235 ± 35 | — | — |
| Me | 392 ± 27 | 435 ± 15 | 152 ± 15 | 298 ± 40** |
| MPO | 215 ± 15 | 175 ± 25 | — | — |
| Ce | 140 ± 10 | 140 ± 10 | — | — |
| GD | 67 ± 17 | 80 ± 10 | 128 ± 8 | 175 ± 25* |
| En | — | — | 212 ± 12 | 345 ± 15** |

*$p < 0.05$
**$p < 0.01$ following Dunn test

NOTES:

The results obtained in the cerebral ageing test show on the one hand the protective action of uridine on cerebral CCK falls, but on the other hand have surprisingly shown that other neurohormones, such as somatostatin, are not protected by administration of the compound.

Therefore, it is to be recognized that uridine is not involved in an aspecific way on all the neurons, but it is selectively involved only for certain neurons which contain CCK as a modulator.

This evidences that uridine shows a pharmacologic effect which is due directly to the protection effected on the neurons in which CCK is present.

2. Tests on pharmacologic action of uridine

The tests hereinafter illustrated show that uridine is able to pharmacologically act through CCK of CNS, on schizophrenia, and moreover in all the cases of an altered balance of the dopaminergic system.

The test was based on the response of dopamine to stimulation with a classic neuroleptic drug.

It is well known that when a neuroleptic drug, i.e. a substance which stimulates neurons, is administered to animals, an over production of DA is observed in the dopaminergic areas of CNS, in that blocking of the dopaminergic receptor stimulates a higher production of the neurotransmitter, which in fact is dopamine. This DA produced in excess is considered to be the cause of the side effects produced by the neuroleptic drugs presently used for the treatment of schizophrenia, and also of the neuron degradation which is observed when such compounds are administered for a long time.

In the following tests, haloperidol was used as a neuroleptic drug. The method and results of the test are described hereinafter.

Four groups of rats CD having eight animals each were treated with uridine (15 mg/kg/die i.p.) and haloperidol (1 mg/kg/die i.p.) with the following treatment schedule. The first group was treated with haloperidol and uridine at the above indicated doses, for fifteen days. Only uridine was administered for the successive six days.

The second group was treated with the same method as the first group, however substituting a saline solution in lieu of uridine, so that group number 2 was treated only with the neuroleptic drug.

Group number 3 substituted saline solution in lieu of haloperidol with respect to group number 1.

Group number 4 was treated with saline solution in substitution both for uridine and haloperidol.

As stated hereinbefore, the treatment with haloperidol was interrupted after 15 days and, after washing out for seven days during which the uridine administration was continued, the animal was anaesthetized. A probe having on its tip a dialysis membrane 2 mm long, was implanted into the striated muscle and continuously perfused with Ringer solution by means of a microinfusion pump.

Samples of perfusate were collected every twenty minutes and immediately analyzed by high pressure liquid chromatography with electrochemical detector and inverted phase column, for the measurement of the DA levels.

Once the stabilization of the measured DA level had been obtained (about 6 samples), haloperidol was administered (2 mg/kg i.p.) and, after 100 minutes, methyl-amphetamine 1.5 mg/kg s.c., in order to evaluate the release of DA by the striatal synaptic terminals.

The test results are referred in Table 2 hereinafter, where the DA levels are expressed in percent of basal values.

TABLE 2

| Time (min) | Administration | DA levels in % of basal level | | | |
|---|---|---|---|---|---|
| | | Group 1 | Group 2 | Group 3 | Group 4 |
| 0 | HP | — | — | — | — |
| 20 | | 100 ± 10* | 125 ± 10* | 95 ± 10* | 200 ± 35 |
| 40 | | 105 ± 15* | 155 ± 10 | 75 ± 5* | 175 ± 15 |
| 60 | | 97 ± 10* | 155 ± 30 | 85 ± 5* | 160 ± 25 |
| 80 | | 98 ± 20* | 125 ± 28 | 90 ± 15* | 170 ± 18 |
| 100 | MAA | 85 ± 10* | 120 ± 18 | 92 ± 10* | 110 ± 10 |
| 120 | | 500 ± 150 | 950 ± 150 | 1000 ± 150 | 1300 ± 500 |
| 140 | | 1000 ± 400 | 1950 ± 350* | 950 ± 200 | 700 ± 200 |
| 160 | | 800 ± 300 | 1650 ± 100* | 850 ± 150 | 550 ± 150 |

*p < 0.05 (Dunn test) in comparison with saline

NOTE:
HP = haloperidol (2 mg/kg, i.p.)
MAA = methylamphetamine (1.5 mg/kg, s.c.)

The results on Table 2 above show that, after administration of haloperidol, both the control animals (group 4) and those chronically treated with haloperidol (group 2) considerably increase the levels of dopamine released into the brain for at least eighty minutes. On the contrary, both the animals treated with uridine, and those treated with uridine and haloperidol, show levels of cerebral dopamine similar to the basal values. This indicates that a chronical administration of uridine is able to "break" the dopamine release effected by haloperidol.

Similarly, it has also shown that through the stimulation by methylamphetamine, a chronical use of uridine is able to block a hyperstimulation of DA release effected by haloperidol (Group 2 versus Group 1).

The above tests on animals have consequently shown that uridine, by increasing the levels of CCK in the brain, improves the dopaminergic functioning and blocks the side effects of neuroleptic drugs, in particular haloperidol.

3. Clinical tests

To evaluate whether the pharmacologic effects of uridine could result in a therapeutical confirmation, the compound was administered to a group of 40 psychotic subjects.

As it is well known in the medical practice that the neuroleptic drugs very often produce side effects of Parkinsonian type, such as rigidity, tremors and the like, and for this reason it is usual to associate antiParkinson drugs to the antipsychotic drugs, the experimental pattern was organized so as to be able to evaluate whether uridine, thanks to its pharmacological properties, was able to be substituted in lieu of the antiParkinson drug normally used.

Twenty psychotic subjects had been under treatment with neuroleptic drugs for various months and with antiParkinsonian drugs because Parkinsonian symptoms had appeared among them. In our test, the antiParkinsonian drug was substituted with uridine. Uridine was administered three times a day as 200 mg pills, along with haloperidol.

In twenty different psychotic subjects the treatment with antiParkinsonian drug was interrupted for two weeks (wash out), before starting a treatment based on uridine and haloperidol, at the same dosages as the above indicated group.

Results

In the first group of subjects, uridine has shown itself able to efficaciously substitute the antiParkinsonian drugs. In fact not one of the subjects has shown Parkinsonian symptoms in the two months period of treatment. In the absence of uridine, the tremor and rigidity symptoms usually appear within two to three weeks.

In the second group the tremor was already evident after the wash out period, before beginning the treatment with uridine.

With this treatment the Parkinsonian symptoms disappeared within the first ten days of treatment, and the symptoms did not reappear until two months after.

It can be concluded that uridine is a drug able to block the symptoms of Parkinson's disease when it is administered alone. Uridine is additionally able to inhibit the side effects of neuroleptic drugs, when it is administered together with the latter in a treatment of psychotic subjects.

The pharmaceutically active agent according to the present invention can be provided for clinical use in pharmaceutical compositions for oral administration under the form of tablets, pills, granules, capsules, drops, syrups and the like together with pharmaceutically acceptable excipients.

Moreover, the pharmaceutically active agent can be administered under the form of a pharmaceutical composition for parenteral administration, in the form of injectable solutes along with known pharmaceutically acceptable vehicles.

A preferred dosage for oral routes is 0.5–5 g/die referred to the pharmaceutically active agent.

We claim:

1. A method for the treatment of Parkinson's disease comprising administering to a patient in need thereof, a therapeutically effective amount of uridine.

2. A method according to claim 1, for blocking the symptoms of Parkinson's disease.

3. A method for the treatment of disorders due to an altered functioning of the cerebral dopaminergic system comprising administering to a patient in need thereof, a therapeutically effective amount of uridine.

4. A method according to claim 3, in which said disorders are due to an altered modulation of the dopamine release in the brain tissue.

5. A method according to claim 4, in which said disorders are due to a low level of cholecystokinin in the brain tissue.

6. A method according to claim 3, in which said administration of uridine produces an increase of the cholecystokinin level in the brain tissue.

* * * * *